United States Patent
Galea et al.

(10) Patent No.: US 9,579,442 B2
(45) Date of Patent: Feb. 28, 2017

(54) ARRAY OF HOLLOW FIBERS AND A SYSTEM AND METHOD OF MANUFACTURING SAME

(71) Applicant: Lung Biotechnology PBC, Silver Spring, MD (US)

(72) Inventors: Anna M. Galea, Stow, MA (US); Kristen LeRoy, Somerville, MA (US); Nicholas Vitale, Albany, NY (US)

(73) Assignee: Lung Biotechnology PBC, Silver Spring, MD (US)

(*) Notice: Subject to any disclaimer, the term of this patent is extended or adjusted under 35 U.S.C. 154(b) by 0 days.

(21) Appl. No.: 14/589,301

(22) Filed: Jan. 5, 2015

(65) Prior Publication Data
US 2015/0202357 A1 Jul. 23, 2015

Related U.S. Application Data

(63) Continuation of application No. 13/506,306, filed on Apr. 10, 2012, now Pat. No. 9,034,083.

(51) Int. Cl.
| | |
|---|---|
| *B01D 53/22* | (2006.01) |
| *B01D 63/02* | (2006.01) |
| *B01D 69/08* | (2006.01) |
| *B01D 19/00* | (2006.01) |
| *A61M 1/16* | (2006.01) |
| *B01D 63/04* | (2006.01) |
| *B01D 67/00* | (2006.01) |
| *B29C 65/48* | (2006.01) |

(52) U.S. Cl.
CPC ....... *A61M 1/1698* (2013.01); *B01D 19/0073* (2013.01); *B01D 53/22* (2013.01); *B01D 53/228* (2013.01); *B01D 63/02* (2013.01); *B01D 63/021* (2013.01); *B01D 63/022* (2013.01); *B01D 63/04* (2013.01); *B01D 67/00* (2013.01); *B01D 69/08* (2013.01); *B29C 65/48* (2013.01); *A61M 2202/0208* (2013.01); *A61M 2202/0225* (2013.01); *B01D 2053/224* (2013.01); *B01D 2325/20* (2013.01)

(58) Field of Classification Search
CPC .. B01D 19/0073; B01D 53/22; B01D 53/228; B01D 2053/224; B01D 63/02; B01D 63/021; B01D 63/022; B01D 63/04; B01D 67/00; B01D 69/08; B01D 2325/20; A61M 1/1698; A61M 2202/0208; A61M 2202/0225; B29C 65/48
USPC .............................................. 96/8; 95/51, 54
See application file for complete search history.

(56) References Cited

U.S. PATENT DOCUMENTS

| | | | |
|---|---|---|---|
| 3,722,695 | A | 3/1973 | Sargent et al. |
| 3,819,442 | A | 6/1974 | Brushenko |
| 4,293,418 | A | 10/1981 | Fujii et al. |

(Continued)

FOREIGN PATENT DOCUMENTS

WO    WO 95/34373    * 12/1995    ............ B01D 69/08

*Primary Examiner* — Jason M Greene
(74) *Attorney, Agent, or Firm* — Foley & Lardner LLP

(57) ABSTRACT

An array of hollow fibers including a plurality of hollow fibers of a predetermined diameter configured to receive a gas having oxygen therein and transfer the oxygen to a fluid and/or transfer carbon dioxide in the fluid to a gas. The array is configured in a predetermined pattern having a predetermined packing density that is a fraction of a total cross-sectional area of the array occupied by the hollow fibers.

6 Claims, 19 Drawing Sheets

(56) References Cited

U.S. PATENT DOCUMENTS

| | | | | |
|---|---|---|---|---|
| 4,427,424 A | * | 1/1984 | Charpin | B01D 59/14 96/8 |
| 4,689,255 A | * | 8/1987 | Smoot | B01D 39/083 210/321.89 |
| 4,906,581 A | * | 3/1990 | Baker | A61M 1/1698 422/108 |
| 5,059,374 A | * | 10/1991 | Krueger | B01D 53/22 210/321.61 |
| 5,270,004 A | * | 12/1993 | Cosentino | A61M 1/1698 128/DIG. 3 |
| 5,429,184 A | * | 7/1995 | Bach | A61M 1/1698 165/149 |
| 5,779,897 A | * | 7/1998 | Kalthod | B01D 53/22 96/8 |
| 5,914,154 A | * | 6/1999 | Nemser | B01D 63/021 427/235 |
| 6,638,479 B1 | * | 10/2003 | Elgas | A61M 1/1698 422/45 |
| 8,580,184 B2 | | 11/2013 | Montoya | |
| 9,034,083 B2 | * | 5/2015 | Galea | B01D 63/02 96/8 |
| 2004/0020845 A1 | * | 2/2004 | Suzuki | B01D 63/021 210/500.23 |
| 2004/0191855 A1 | * | 9/2004 | Leukes | C12M 29/16 435/41 |
| 2009/0200695 A1 | | 8/2009 | Schafer et al. | |
| 2010/0050875 A1 | * | 3/2010 | Ziembinski | A61M 1/1698 96/8 |
| 2010/0282680 A1 | | 11/2010 | Su et al. | |
| 2012/0234745 A1 | | 9/2012 | Jerman et al. | |
| 2014/0014568 A1 | | 1/2014 | Sternberg | |

* cited by examiner

… (1)

ARRAY OF HOLLOW FIBERS AND A SYSTEM AND METHOD OF MANUFACTURING SAME

RELATED APPLICATIONS

This application is a continuation of U.S. patent application Ser. No. 13/506,306, filed Apr. 10, 2012 which hereby claims the benefit of and priority thereto under 35 U.S.C. §§119, 120, 363, 365, and 37 C.F.R. §1.55 and §1.78, and is incorporated herein by reference.

GOVERNMENT RIGHTS

This invention was made with United States Government support under 6R43HL074456-02 and 1R43HL091593-01, both awarded by the National Institutes of Health. The United States Government has certain rights in the invention.

FIELD OF THE INVENTION

This invention relates to an improved array of hollow fibers and a system and method for manufacturing same.

BACKGROUND OF THE INVENTION

Conventional hollow fiber oxygenators may be used to oxygenate the blood for patients suffering with diseased or damaged lungs. One conventional oxygenator, often referred to as a wrapped hollow fiber oxygenator, relies on hollow fibers wrapped around a hollow core. The wrapped design often results in a random or irregular spacing of the hollow fibers. Additionally, because the hollow fibers are wrapped about a hollow core, there is a relatively large amount of void space in the oxygenator. Such a design may compromise the efficiency of the oxygenator.

Another conventional oxygenator, often referred to as a bundled oxygenator, relies on an array of hollow fibers bundled together potted in glue at each end. The glue is then cut to form a header on each end of the array. The bundling design of the array typically results in a random arrangement of hollow fiber which prevents the hollow fibers from being packed closely and in a regular pattern which may compromise the efficiency of the oxygenator.

BRIEF SUMMARY OF THE INVENTION

This invention features an array of hollow fibers including a plurality of hollow fibers of a predetermined diameter configured to receive a gas having oxygen therein and transfer the oxygen to a fluid and/or transfer carbon dioxide in the fluid to a gas. The array is configured in a predetermined pattern having a predetermined packing density that is a fraction of a total cross-sectional area of the array occupied by the hollow fibers.

In one embodiment, the array may be configured such that the distance between the hollow fibers is less than or substantially equal to the predetermined diameter. The predetermined packing density of the array may be configured to be a fraction of the total cross-sectional area of the array occupied by the plurality of hollow fibers. The fraction may be in the range of 0.20 to about 0.90. The predetermined diameter may be less than or equal to about 0.2 mm. The plurality of hollow fibers may be configured in a hexagonal arrangement. The plurality of hollow fibers may be configured to be hexagonally closely packed. The array may include a plurality of headers configured to align the plurality of hollow fibers in the predetermined orientation.

This invention features a method for manufacturing an array of hollow fibers, the method includes: a) providing an array manufacturing device including a base defining a bed and an adhesive applicator receivable in the base, b) providing a plurality of shims each configured to fit into the bed, c) providing a plurality of layers of hollow fibers, d) placing the plurality of shims into the bed, e) applying adhesive to the applicator, f) positioning the applicator to contact and distribute the adhesive to a top shim of the plurality of shims in the bed, g) placing a first layer of hollow fibers over the top shim with adhesive thereon, h) rolling the adhesive away from a center portion of the first layer of hollow fibers, i) removing one of the plurality of shims from the bed, j) placing another layer of hollow fibers over the first layer of hollow fibers, k) applying adhesive to the adhesive applicator, l) positioning the applicator to contact and distribute the adhesive to the next layer of hollow fibers, m) rolling the adhesive away from a center portion of the next layer of hollow fibers, and n) repeating at least steps i) through m) until an array having a predetermined number of layers is formed.

In one embodiment, the adhesive applicator may include a plurality of blades and step of applying the adhesive may include applying the adhesive to the blades. Each of the blades may include a contact surface and the step of applying the adhesive may include applying the adhesive to the contact surface. The method may include the step of pivotably attaching the adhesive applicator to the base. The method may include the step of providing a roller to roll the adhesive away from the center portion. The method may include the step of trimming excess adhesive from a completed array of hollow fibers.

This invention also features a method for manufacturing an array of hollow fibers, the method including: a) providing an array manufacturing device including a base defining a bed with opposing sides an adhesive applicator receivable in the base, b) providing a plurality of shims each sized to fit the opposing sides, c) providing a plurality of layers of hollow fibers, d) placing a pair of opposing shims adjacent to the opposing sides, e) placing a layer of hollow fibers between the opposing shims, f) applying adhesive to the opposing shims and the layer of hollow fibers, g) rolling the adhesive away from a center portion of the layer of hollow fibers, and h) repeating at least steps d) through g) until an array having a predetermined number of layers of hollow fibers is formed.

In one embodiment, the method may include the step of pivotably attaching the adhesive applicator to the base.

This invention further features a method of manufacturing an array of fibers, the method including: a) providing a plurality of layers of hollow fibers, b) providing first and second end-headers each including a plurality of recesses on one side configured to fit a layer of the plurality of hollow fibers, c) providing a plurality of mid-headers each including a plurality of recesses on both sides configured to fit a layer of the plurality of hollow fibers, d) applying adhesive to one end-header and one mid-header, e) sandwiching one layer of the plurality of hollow fibers between the end-header and the mid-header, f) applying adhesive to another mid-header, g) sandwiching another layer of hollow fibers between two mid-headers, h) repeating steps f) and g) a predetermined number of times, i) applying adhesive to the second end-header, and j) sandwiching a final layer of hollow fibers between the end-header and a last mid-header.

This invention also features a system for manufacturing an array of hollow fibers. The system includes an array manufacturing device including a base defining a bed and an adhesive applicator receivable in the base, a plurality of shims each configured to fit into the base, a plurality of layers of hollow fibers sized to fit into the base, and a roller.

In one embodiment, the adhesive applicator may include opposing arms and a plurality of blades therebetween. Each of the blades may include an adhesive contact surface. The adhesive applicator may be pivotably attached to the base. The method may include each of the plurality of shims may have a thickness approximately equal to the thickness of one of the plurality of layers of hollow fibers. The plurality of blades may form a predetermined shape. The predetermined shape may include the shape of a lung or a rectangular shape.

This invention also features a system for manufacturing an array of hollow fibers. The system includes an array manufacturing device including a base defining a bed with opposing sides an adhesive applicator receivable in the base, a plurality of layers of hollow fibers, a plurality of shims each sized to fit the opposing sides, and a roller.

In one embodiment, the method may include the step of pivotably attaching the adhesive applicator to the base.

BRIEF DESCRIPTION OF THE SEVERAL VIEWS OF THE DRAWINGS

Other objects, features and advantages will occur to those skilled in the art from the following description of the embodiments and the accompanying drawings, in which.

DETAILED DESCRIPTION OF THE INVENTION

Figure 1:
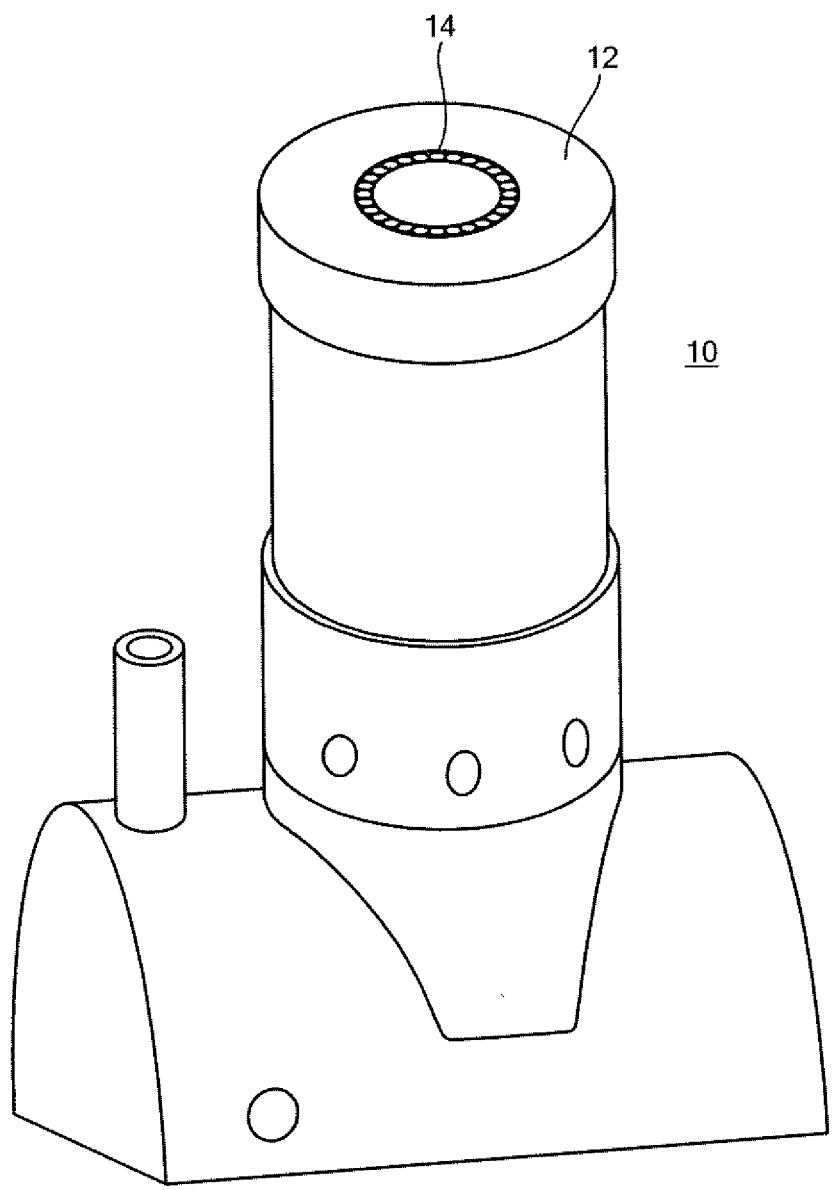
FIG. 1 is a three-dimensional view showing one example of a conventional wrapped hollow fiber oxygenator.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one example of conventional wrapped oxygenator 10 which may be used to receive a gas having oxygen therein and transfer the oxygen to a physiological fluid. As discussed in the Background section above, conventional wrapped oxygenator includes hollow fibers 12 wrapped about hollow core 14. However, such a design often results in random or irregular spacing of the hollow fibers and produces a large amount of void space which may compromise the efficiency of oxygenator 10.

Figure 2:
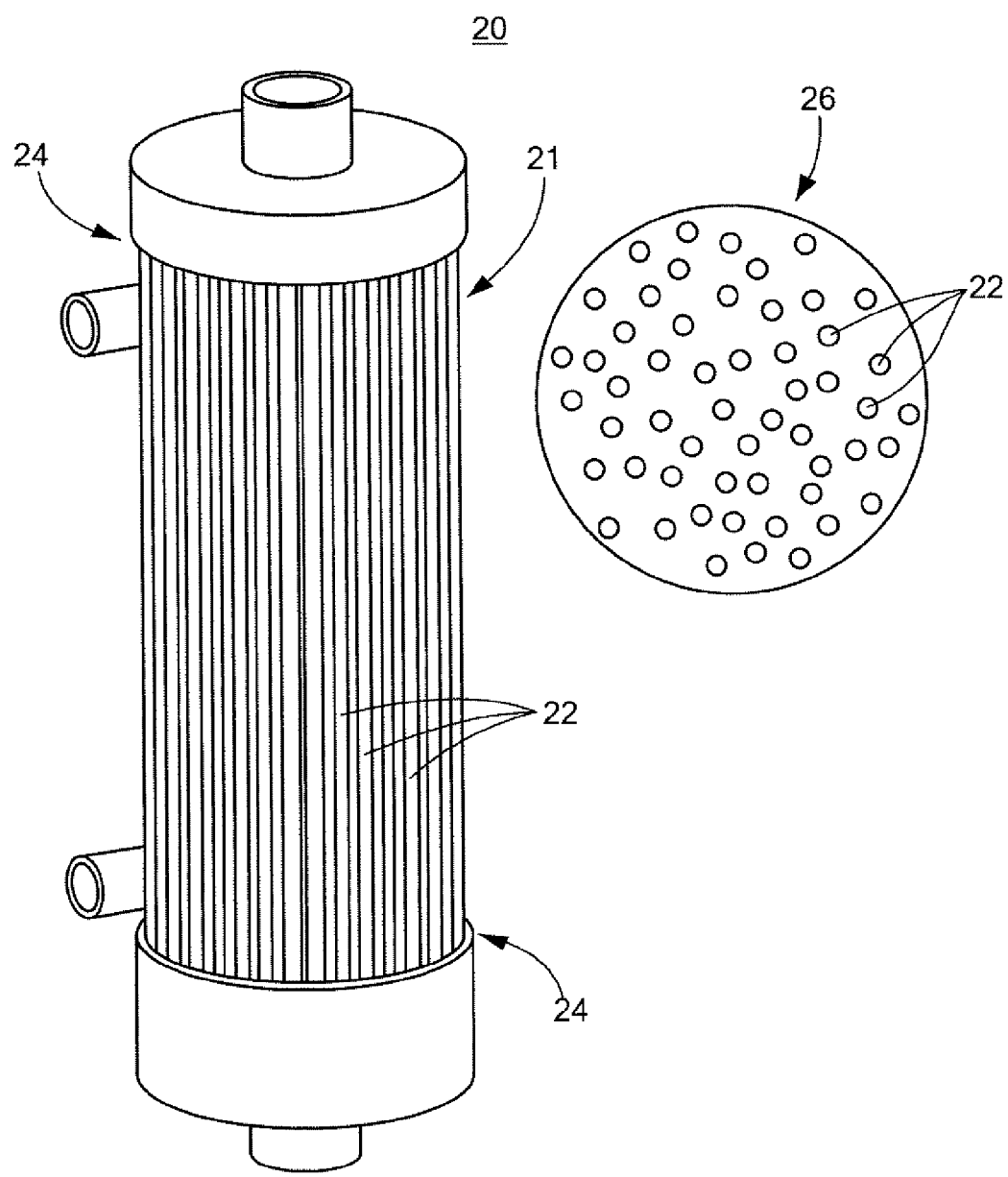
FIG. 2 is a three-dimensional view showing one example of a conventional bundled hollow fiber oxygenator.
Figure 3:
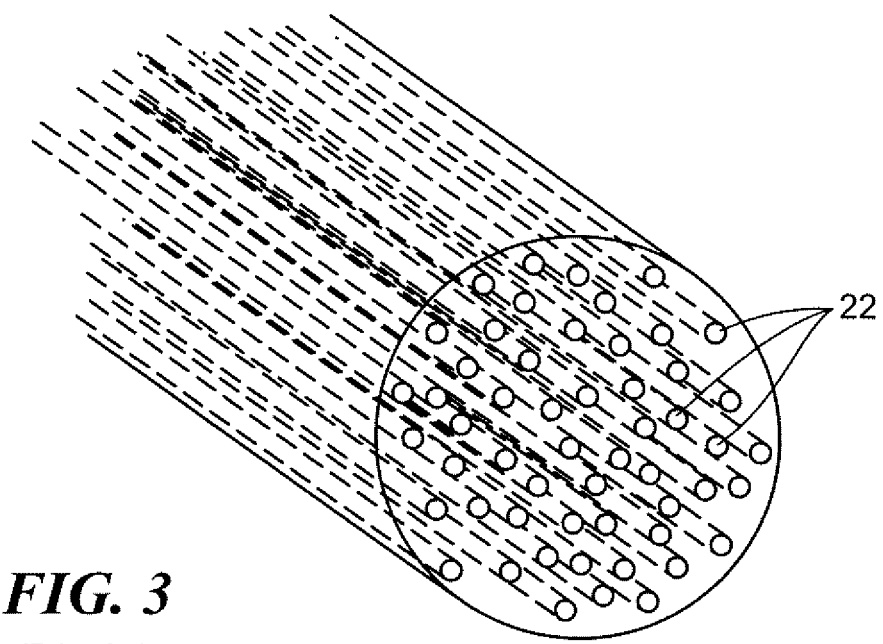
FIG. 3 is a schematic view showing in further detail the random arrangement of the hollow fibers of the bundled oxygenator shown in FIG. 2.

Conventional bundled oxygenator 20, FIG. 2, includes array 21 of hollow fibers 22 bundled together in potting glue 24. The glue is then cut to form a header on each end of array 21. However, the bundling design typically results in a random arrangement of hollow fibers 22, e.g., as indicated at 26. This prevents fibers 22 from being packed closely and in a regular pattern which may compromise the efficiency of oxygenator 20. FIG. 3 shows a more detailed view of the random or irregular arrangement of hollow fibers 22.

Thus, conventional wrapped oxygenator 10, FIG. 1, and bundled oxygenator 20, FIG. 2, may not provide a sufficient density of hollow fibers to effectively oxygenate blood or similar type physiological fluid.

Figure 4:
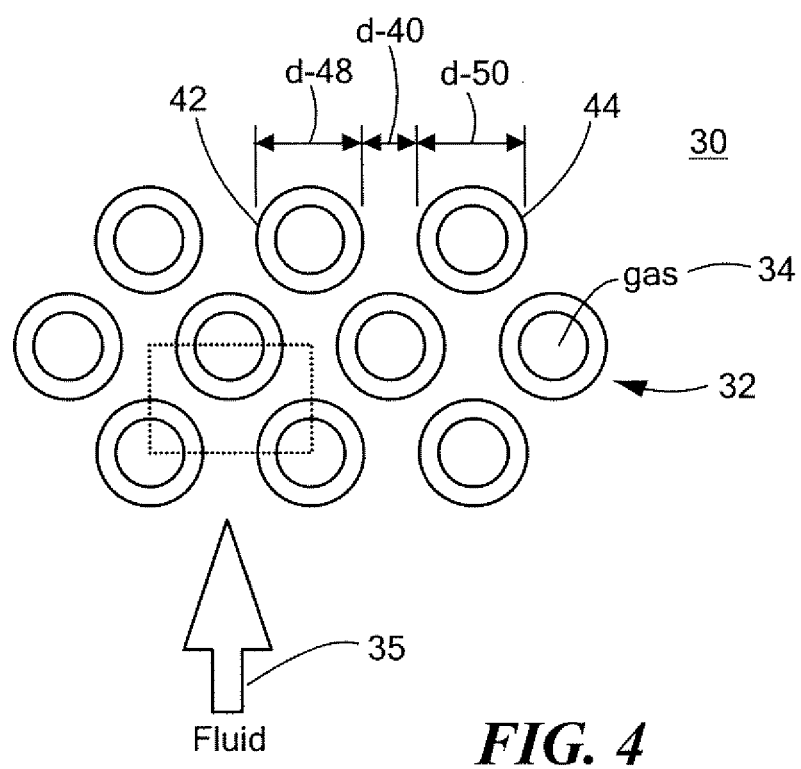
FIG. 4 is a schematic end-view showing one example of the array of hollow fibers in accordance with one embodiment of this invention.

In contrast, array 30, FIG. 4 of one embodiment of this invention, includes a plurality of fibers 32 each having a predetermined diameter, e.g., outer diameter d-48 of fiber 42 and outer diameter d-50 of fiber 44. Fibers 32 are each configured to receive a gas, e.g., exemplary gas 34, such as ambient air, an oxygen gas, or any gas having oxygen therein, and transfer the oxygen in the gas to a fluid 35 and/or transfer carbon dioxide in fluid 35 to gas 34. The fluid which may be a physiological fluid, such as blood or plasma or similar type physiological fluid, or it may be an organic or inorganic fluid. Array 30 is configured in a predetermined pattern with a predetermined packing density. For example, array 30 may be configured such that the distance between hollow fibers 32 is less than or substantially equal to the diameter of the hollow fibers 32. In one design, distance d-40 between hollow fibers 42 and 44 is less than the diameter d-48 of fiber 42 and the diameter d-50 of hollow fiber 44. Hollow fibers 32 preferably have a diameter of about 0.2 mm, although the diameter may be larger or smaller than 0.2 mm. The result is fibers 32 of array 30 provide for an increased packing density of hollow fibers in array 30 when compared to the conventional oxygenators or similar type arrays of hollow fibers.

Figure 5A:
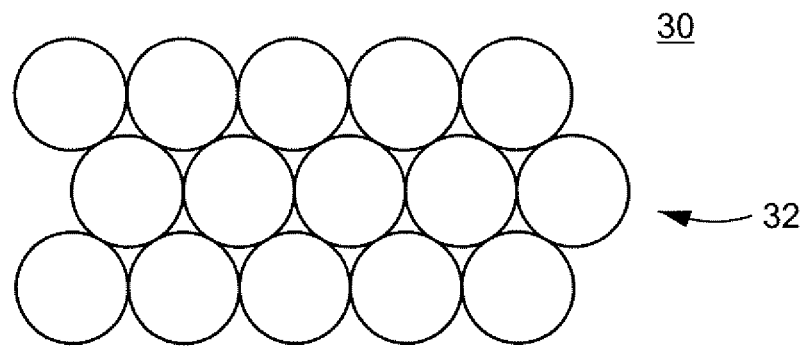
FIG. 5A is a schematic end-view showing one example of an array of hexagonally closely packed hollow fibers in accordance with one embodiment of this invention.
Figure 5B:
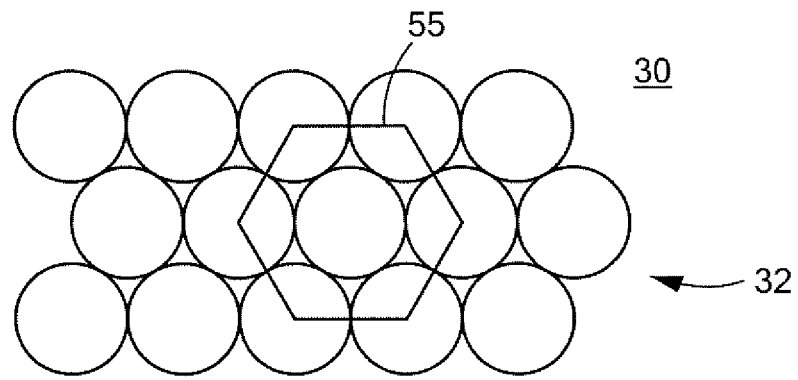
FIG. 5B is a schematic end-view showing an example an imaginary hexagon in the array shown in FIG. 5A.
Figure 5C:
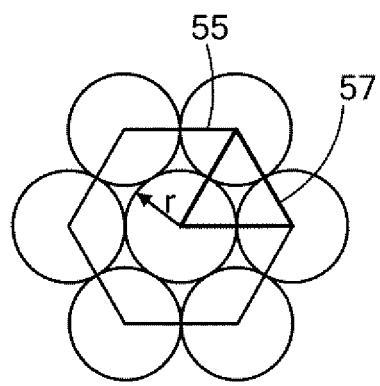
FIG. 5C is a schematic end-view of a depiction of triangles within the hexagon shown in FIG. 5B which may be used to calculate the fraction of the area of the array occupied by the plurality of hollow fibers in accordance with one embodiment of this invention.

In one example, array 30 includes a plurality of hollow fibers 32 that are configured to be hexagonally closely packed, e.g., as shown in FIG. 5A. This is often referred to hexagonally closely packed because one can imagine space-filling hexagons overlapping the circular cross-sections of plurality of hollow fibers 32 with the vertices of hexagons at the center of each of the circular-shaped plurality of fibers, e.g., hexagon 55, FIG. 5B. A closer look at a portion of hexagon 55, FIG. 5C, shows that there may be triangles, e.g., exemplary triangle 57, that are also space filling and can represent a unit-cell in which the area fraction can be calculated using the formula:

$$AF = \frac{A_{circ}}{A_{tri}} = \frac{\pi r^2}{2\sqrt{3r*r}} \quad (1)$$

In one embodiment, the predetermined packing density of array 30, FIGS. 4 and 5, is configured to be a fraction of the total cross-sectional area of array 30 occupied by the plurality of hollow fibers 32. In this example, the fraction is calculated using equation (1) above. As discussed above, array 30 may be configured such that the distance between hollow fibers 32 is less than or substantially equal to the diameter of the hollow fibers 32. In this case, the calculated fraction using equation (1) above is approximately 0.22. In another example, when the spacing between the plurality of hollow fibers 32 is approximately one half of the diameter for each of the plurality of hollow fibers, the calculated fraction is about 0.40. In another example, there may be zero spacing between the plurality of hollow fibers, e.g., as shown in FIG. 5, a true hexagonal closely packed arrangement. In this example the calculated fraction is about 0.90.

In another example, the density of hollow fibers 32 of array 30 may be greater than or equal to about 7.2 fibers/mm². In one example, the calculation for a density of 7.2 fibers/mm² is discussed below with reference to FIG. 6. In this design, array of hollow fibers 32 includes seven fibers, 60, 62, 64, 66, 68, and 70 arranged in a hexagonal configuration with fiber 72 in the center. In one example, the diameter, d, for each of fibers 60-72 is about 0.2 mm, exemplary indicated by d-74 for fiber 72. As known by those skilled in the art, the area of hexagon 76 is computed by the following formula:

$$A = (1.5\sqrt{3})*t^2 \quad (2)$$

where t is equal to the length of the sides of hexagon 76, e.g., indicated by t-78. The length t is equal to twice the diameter, (2 d), of a hollow fiber, e.g., indicated at 77. Thus, equation (1) now becomes:

$$A = 1.5\sqrt{3}*(2d)^2 \sim = 2.6*(2d)^2 \quad (3)$$

which equals:

$$A = 6\sqrt{3}*(2d)^2 \sim = 10.4*d^2 \quad (4)$$

Figure 6:
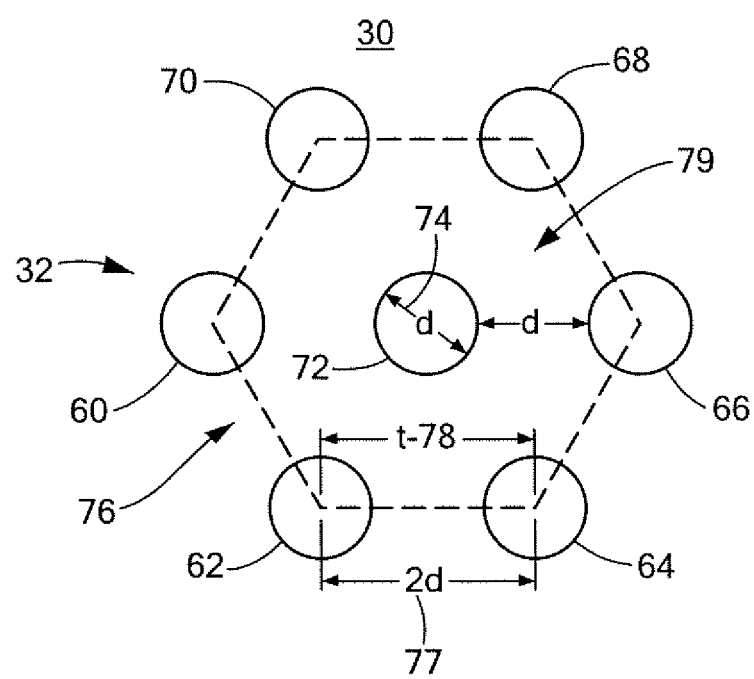
FIG. 6 is a schematic end-view showing one example of the distance between exemplary hollow fibers used to calculate one example of the predetermined density of one embodiment of the array of hollow fibers of this invention.

As shown in FIG. 6, there are 3 fibers of diameter d in the area 79 of hexagon 76, that are no larger than 10.4 d². That is, each of the six hollow fibers 60-70 includes ⅓ of the area of a hollow fiber totaling 2 hollow fibers plus hollow fiber 72 in the center. This results in a density of no less than:

$$\text{Density of hollow Fibers of array 3} \frac{3}{(10.4)*(0.2 \text{ mm})^2} \text{fibers/mm}^2 \quad (5)$$

which equals 7.2 fibers/mm². The size of hollow fibers 32 and distance therebetween may be even smaller than 0.2 mm so the density of hollow fibers 32 of array 30 may be even higher. The increased density of the hollow fibers of the array of one or more embodiments of this invention provides an approximately hexagonally closely packed arrangement of the hollow fibers. The result is array 30 more efficiently oxygenates a fluid than the conventional oxygenators or similar type devices.

Figure 7:
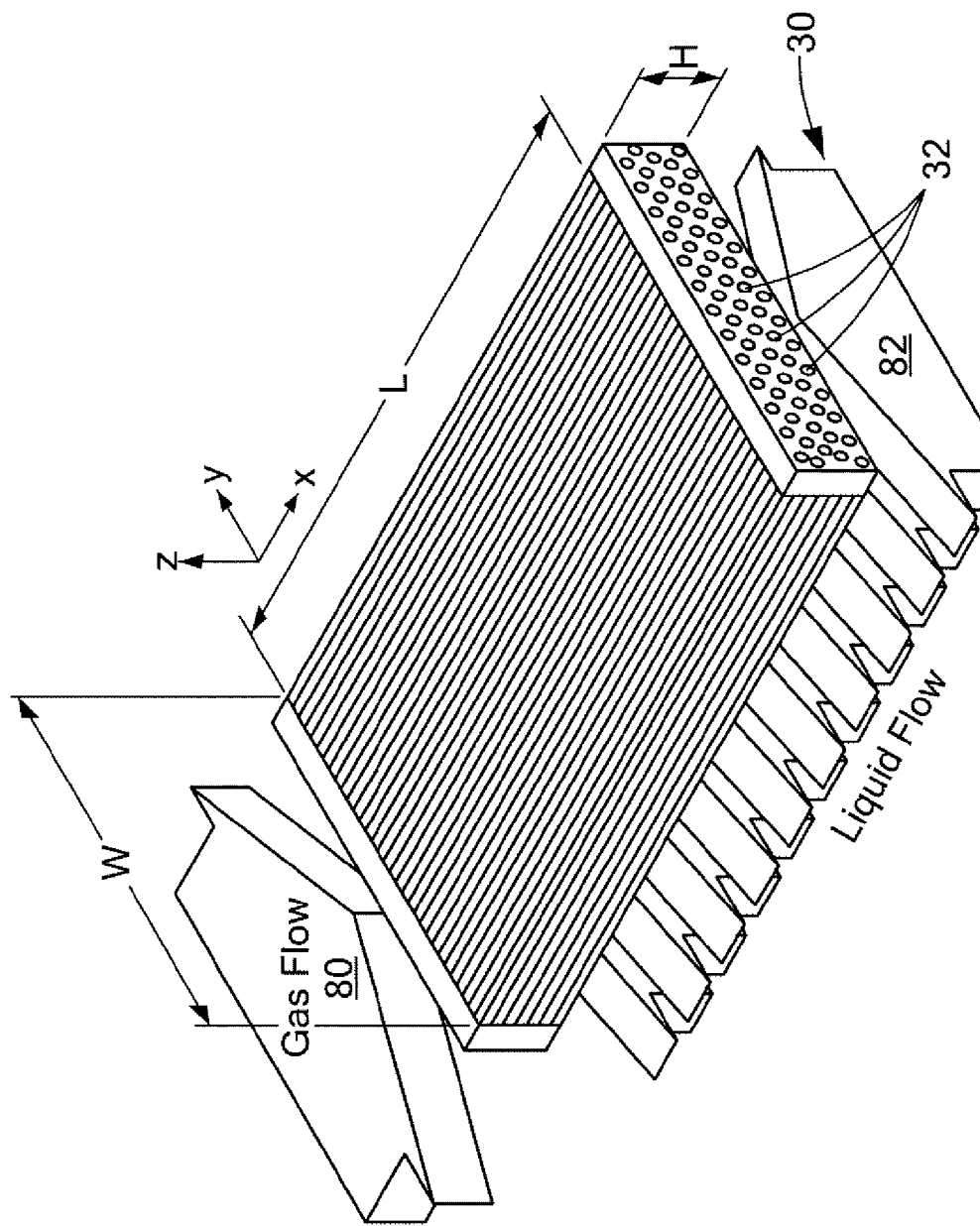
FIG. 7 is a three-dimensional view showing one embodiment of an array of hollow fibers of this invention used to oxygenate a fluid.

FIG. 7 shows one example of array 30 having a plurality of fibers 32 having the increased packing density as discussed above with reference to one or more of FIGS. 4-6. In this example, array 30, FIG. 7, is configured to receive gas flow 80, e.g., ambient air, an oxygen gas, or any gas having oxygen therein, and a flow of fluid 82, e.g., blood or plasma or similar type physiological fluid, or an organic or inorganic fluid, and is designed to transfer the oxygen in gas 80 to fluid 82 and/or transfer carbon dioxide in fluid 82 to gas 80.

Figure 8:
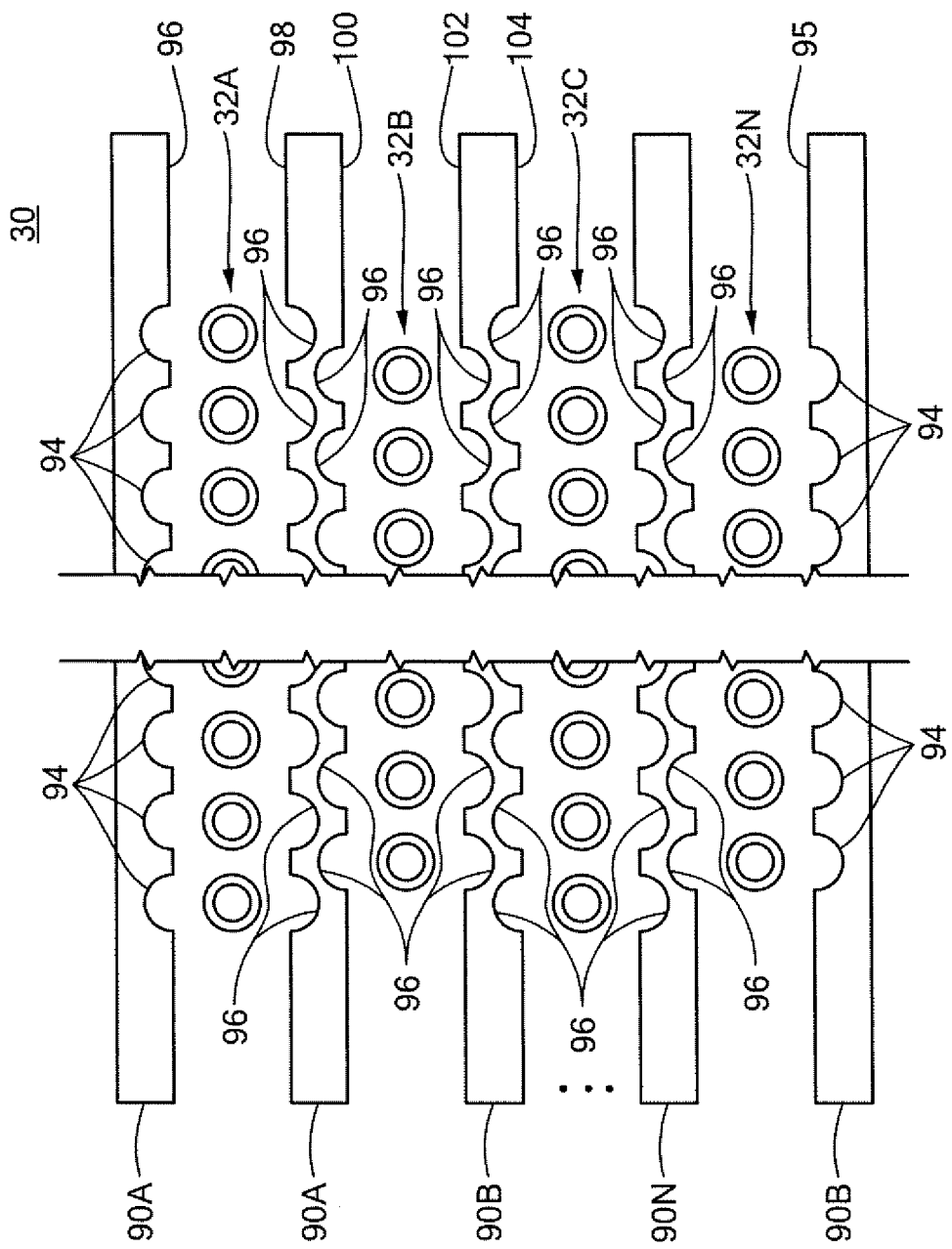
FIG. 8 is a schematic end-view showing one example of headers which may be used to align the hollow fibers shown in FIG. 4 in accordance with one embodiment of this invention.

In one example, array 30, FIG. 8 may include end-headers 90A, 90B, and one or more mid-headers, e.g., mid-headers 92A, 92B . . . 92N, which align hollow fibers 32 in the closely packed configuration with increased density discussed above with reference to FIG. 4. End-headers 90A, 90B, FIG. 8, and mid-headers 92A, 92B . . . 92N include recesses 94, 96, respectively, which preferably align hollow fibers 32 of array 30 such that the distance between hollow fibers 32 is smaller than or equal to the diameter of fibers, as discussed above with reference to FIG. 4.

One method for manufacturing the array 30 of hollow fibers 32 uses end-headers 90A, 90B, FIG. 8, and one or more mid-headers 92A, 92B . . . 92N. In one example, a biocompatible adhesive is dispensed to side 95 of end-header 90A. Layer of hollow fibers 32A is then fitted into recesses 94. The biocompatible adhesive is then applied to side 98 of mid-header 92A. Recesses 96 of mid-header 92A are fitted over layer of hollow fibers 32A already fitted into recesses 94 of end-header 90A. Mid-header 92A is then pressed to contact end-header 90A and sandwich layer of hollow fibers 32A therebetween. Next, adhesive is applied to the side 100 of mid-header 92A and layer of hollow fibers 32B is fitted into recesses 96. Adhesive is applied to the next mid-header, e.g., side 102 mid-header 92B and it is pressed to contact and mid-header 92A and sandwich layer of hollow fibers 32B therebetween. Adhesive is applied to side 104 of mid-header 92B and layer of hollow fibers 32C and is fitted into the recess 96 of mid-header 92B. The process of adding mid-headers and layers of hollow fibers 32 is repeated until the desired number of layers of hollow fibers 32 is achieved, e.g., about twenty-five to thirty-five layers. Then adhesive is applied to end-header 90B and it is pressed to contact the last mid-header and sandwich hollow fibers 32N therebetween. The adhesive is then allowed to cure to complete the process.

Figure 9:
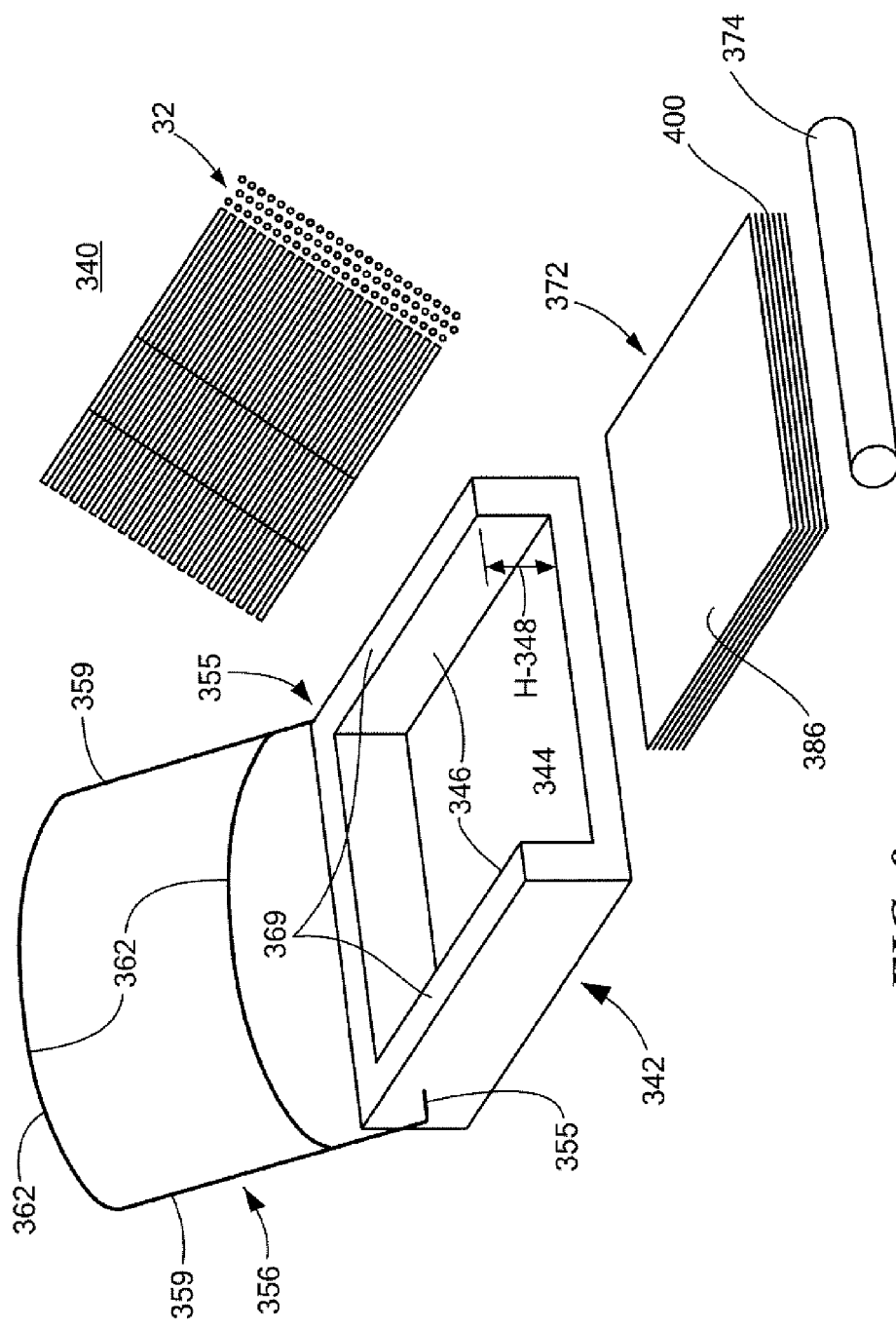
FIG. 9 is a three-dimensional view of one embodiment of a system of this invention used to manufacture the array of hollow fibers shown in FIG. 4.

Another method for manufacturing an array 30, FIG. 4 of hollow fibers 32, may include system 340, FIG. 9. In this example, the method is semi-automated to allow for repeatable application of a uniform amount of the biocompatible adhesive and alignment each layer of the hollow fibers such that the spacing therebetween remains relatively constant.

Figure 10:
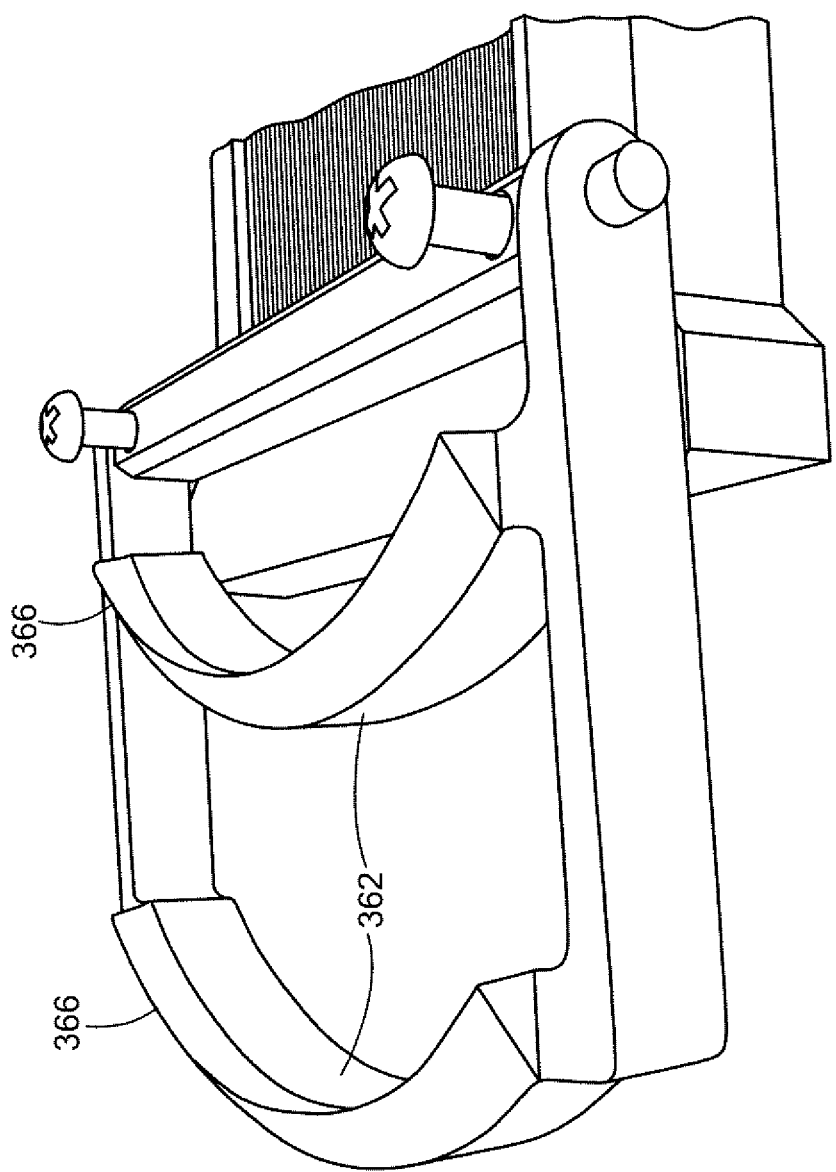
FIG. 10 is a side-view showing in further detail the structure of the adhesive applicator shown in FIG. 8.

System 340, FIG. 9, includes array manufacturing device 342. Device 342 includes base or bed 344 with sides 346. Sides 346 have a height, H-348, which is approximately equal to the final height of the array, typically 8 to 15 mm. H-348 is approximately equal to height of about twenty-five to thirty-five stacked layers of hollow fibers 32 for a typical array being manufactured, e.g., as shown in FIG. 7. System 340 also includes adhesive applicator 356. Applicator 356 includes opposing arms 359 with blades 362 therebetween. Arms 369 are pivotably attached to sides 346 of device 342, e.g., with hinge 355. Blades 362, FIG. 10, each preferably include contact surface 366.

Figure 11:
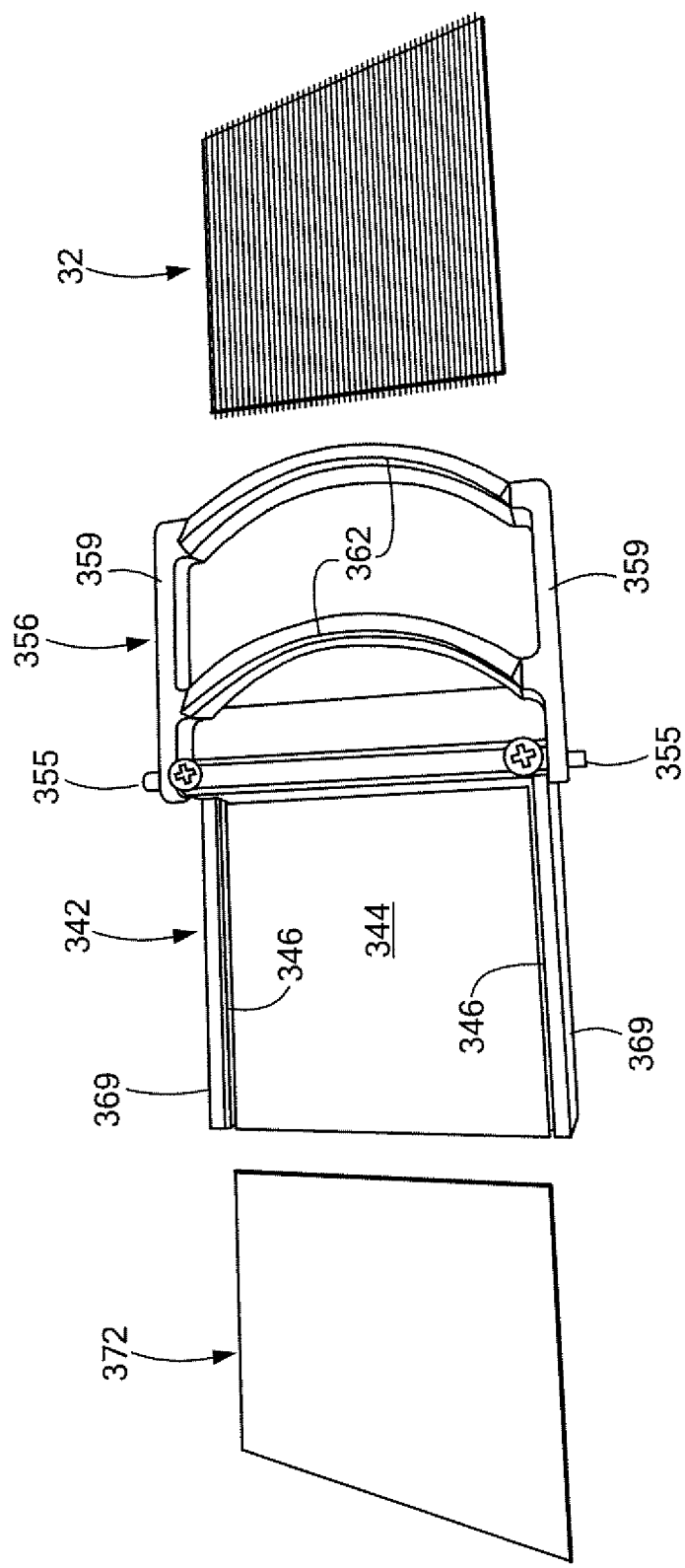
FIG. 11 is a more detailed three-dimensional view of the system shown in FIG. 8.

System 340, FIG. 9, also includes a plurality of layers of hollow fibers 32, e.g., about twenty-five to thirty-five layers of hollow fibers 32, although any number of layers of hollow fibers 32 may be used depending on the size of the array of hollow fibers needed. Hollow fibers 32, FIG. 9, are commercially available from, e.g., Dainippon Ink and Chemical Inc. (DIC), Japan. System 340 also includes a plurality of shims 372. Each of shims 372 is typically as thick as each layer of hollow fibers 32, e.g., about 0.2 mm. Each of shims 372 is sized to fit into bed 344. System 340 also preferably include smooth roller 374. FIG. 11 shows are more detailed view of device 342 with adhesive applicator 356, shims 372, and one layer of hollow fibers 32.

One example of the method of manufacturing an array of hollow fibers in accordance with this invention is discussed below with reference to FIGS. 9-18. In this example, plurality of shims 372, FIGS. 9 and 11, are placed into bed 344 of device 342, step 380, FIG. 12. Preferably, a sufficient number of shims is used such that top shim 386 is coplanar with top surface 369 of sides 346. Next, adhesive 382, e.g., Silastic® silicone adhesive (Dow Corning), is applied to contact surface 366 on blades 362, step 384. Adhesive applicator 356 is then lowered such that contact surface 366 with adhesive 382 thereon contacts top shim 386, step 390, FIG. 13. This applies adhesive 382 in the shape of blades to top shim 386.

Figure 14:
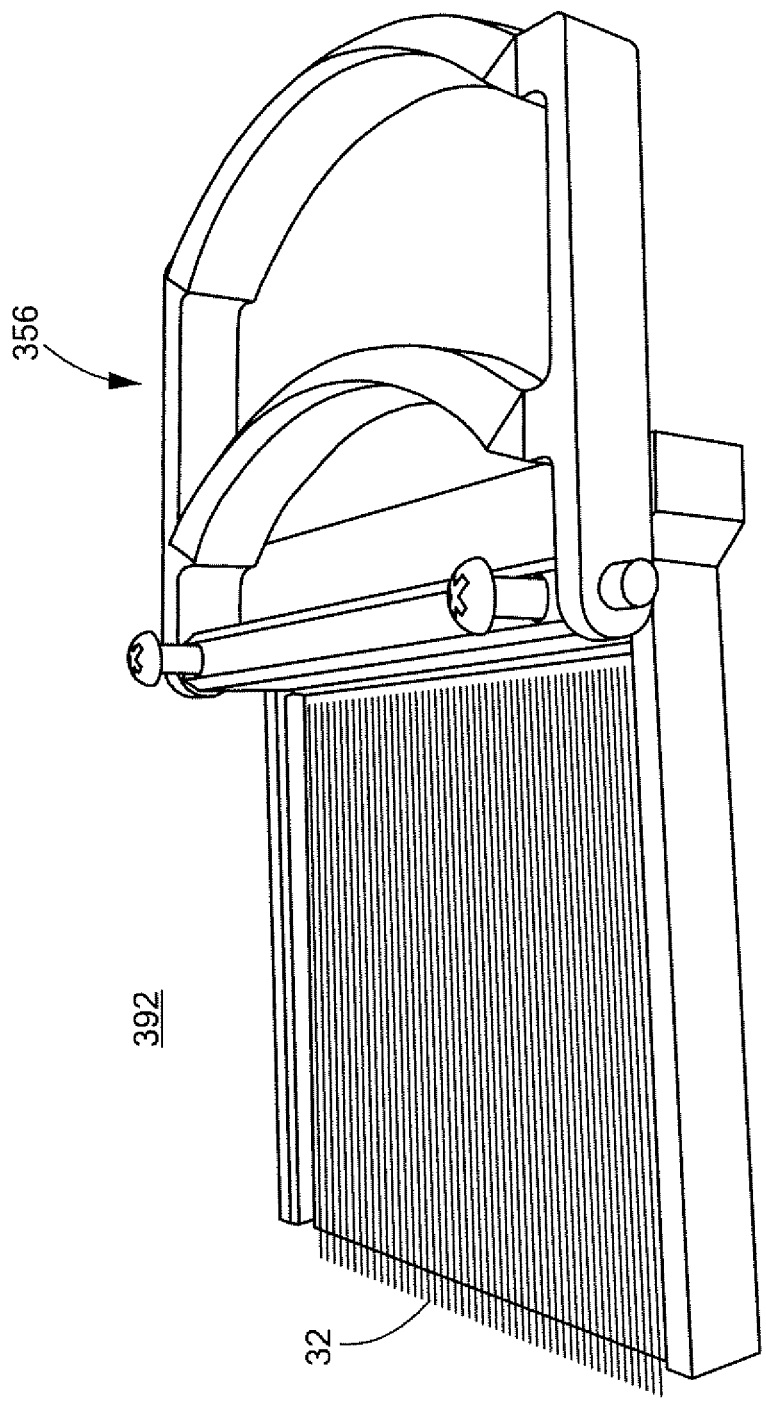
Figure 15:
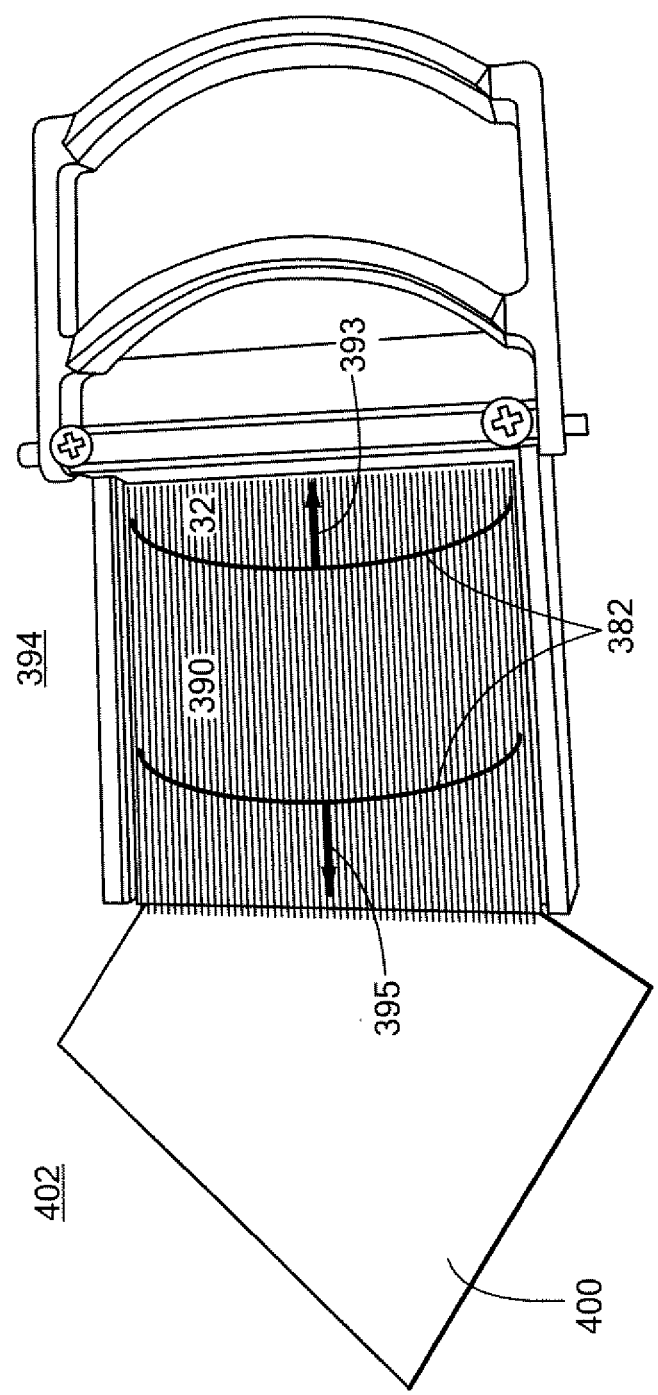
Figure 16:
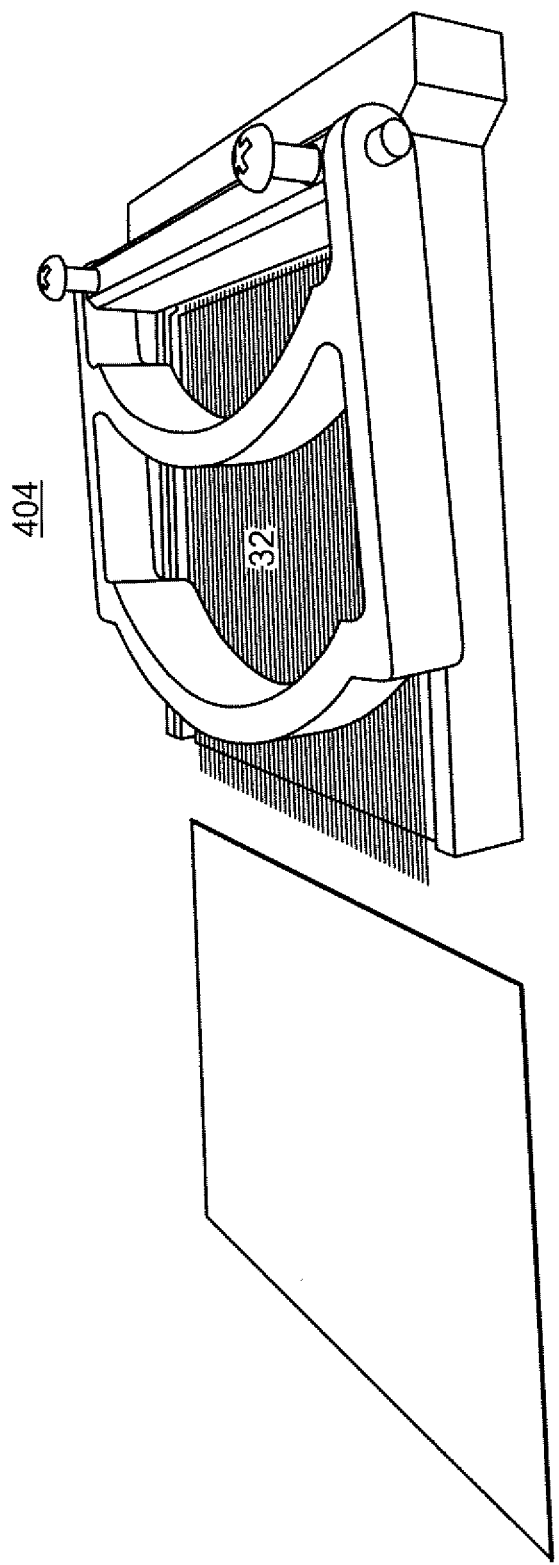

Applicator 356 is then raised and a layer of hollow fibers 32 is placed over top shim 386, step 392, FIG. 14. FIG. 15 shows an example of layer of hollow fibers 32 in place over adhesive 382. Adhesive 382 is then rolled away from the center portion 390 of hollow fibers 32 using roller 374, FIG. 9, step 394, FIG. 15. Step 394 preferably includes spreading adhesive 382 outwards and away from center area 390, e.g., the direction shown by arrows 393, 395.

Figure 17A:
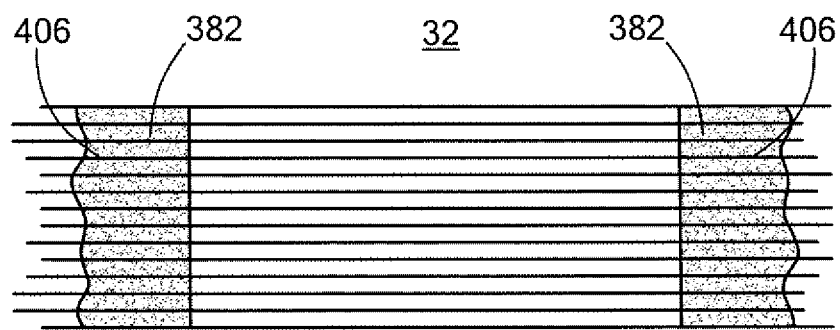
Figure 17B:
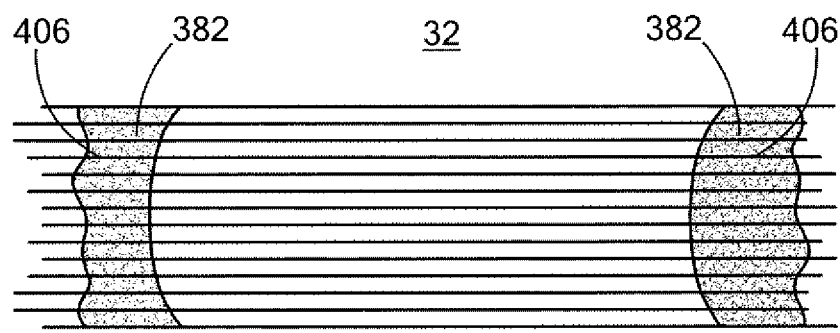
Figure 18A:
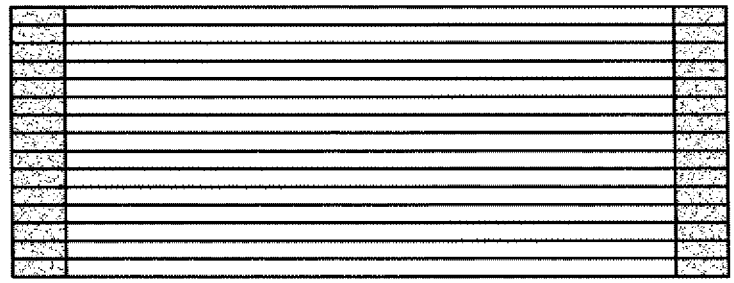
Figure 18B:
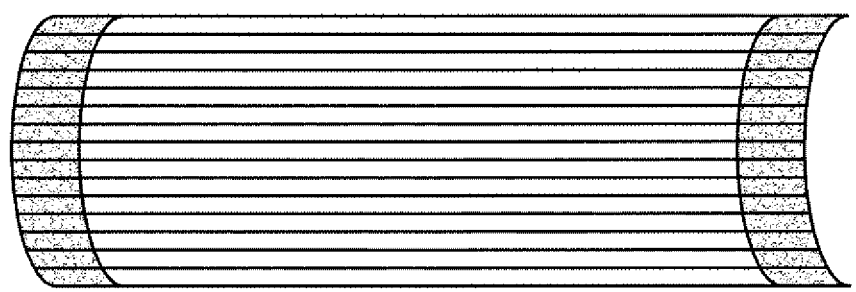

Next, one of the plurality of shims 372, e.g., bottom shim 400, FIGS. 9 and 15, is removed from bed 344, FIG. 9 in step 402, FIG. 15. This causes the top of array 30 of hollow fibers 32 being manufactured to stay at the same height, e.g., H-348, FIG. 9, as each new layer of hollow fibers 32 is added. Then, adhesive 382, FIG. 12, is again applied to contact surface 366 on blades 362. Another layer of hollow fibers 32 is placed over top shim 386. Adhesive applicator 356 is then lower in position over the next layer of hollow fibers 32, step 404, FIG. 16. Step 394 (rolling the adhesive) is then repeated. Steps 384 and steps 392 through 404 are repeated as many times as needed until an array with the desired numbers of layers of hollow fibers is formed, e.g. about twenty-five to thirty-five layers. After the array of hollow fibers is complete, the adhesive is allowed to cure. Excess adhesive 406, e.g., FIGS. 17*a*-17*b* is then trimmed, as shown in FIGS. 18*a*-18*b*.

Although as discussed above with reference to FIGS. 9-18*b*, adhesive applicator with blades 362 has a shape resembling a lung, this is not a necessary limitation of this invention. In other designs, adhesive applicator with blades 362 may have any shape known to those skilled in the art to form an array of hollow fibers of any various shape.

Figure 12:
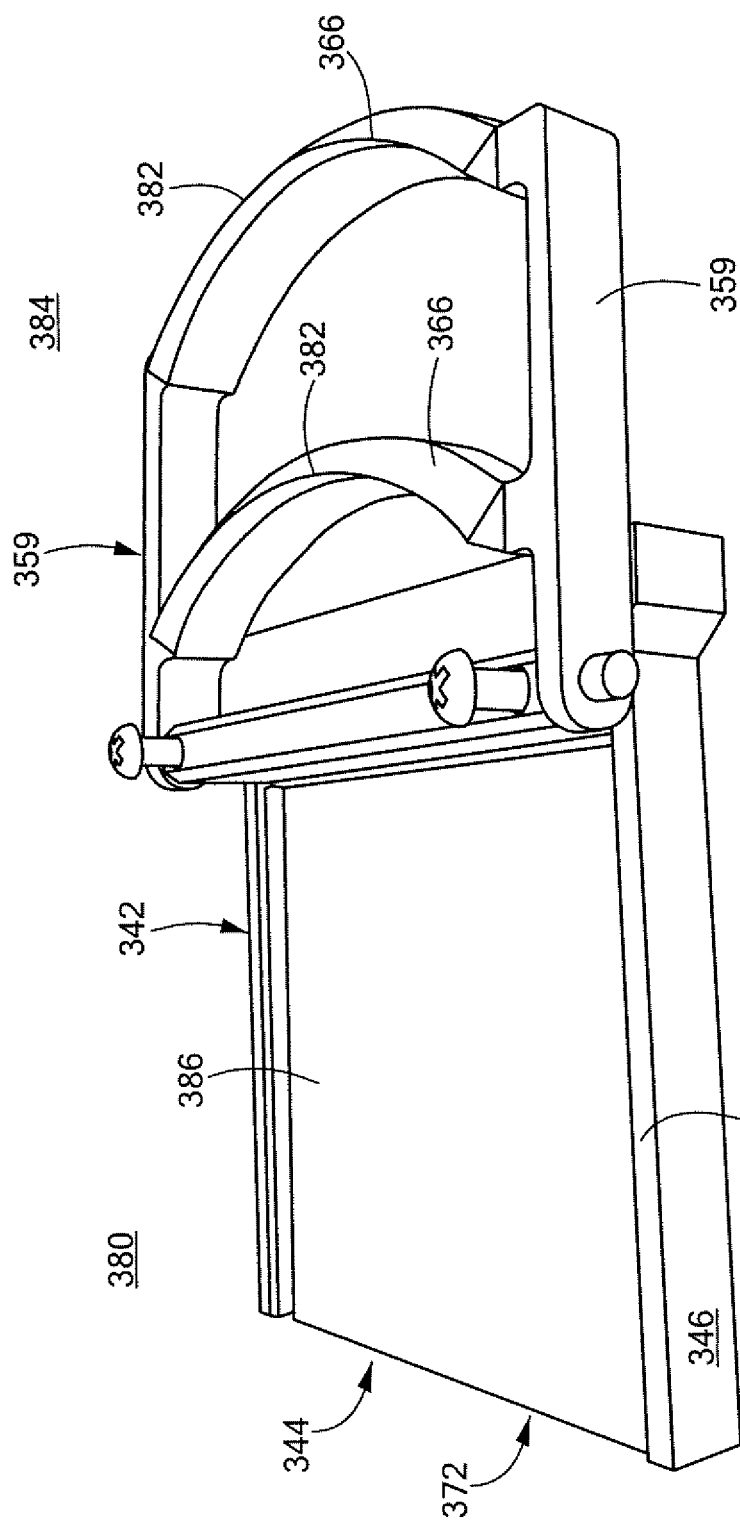
FIGS. 12-18b show one example of the steps used to manufacture the array of hollow fibers shown in FIG. 4 in accordance with one embodiment of this invention.
Figure 13:
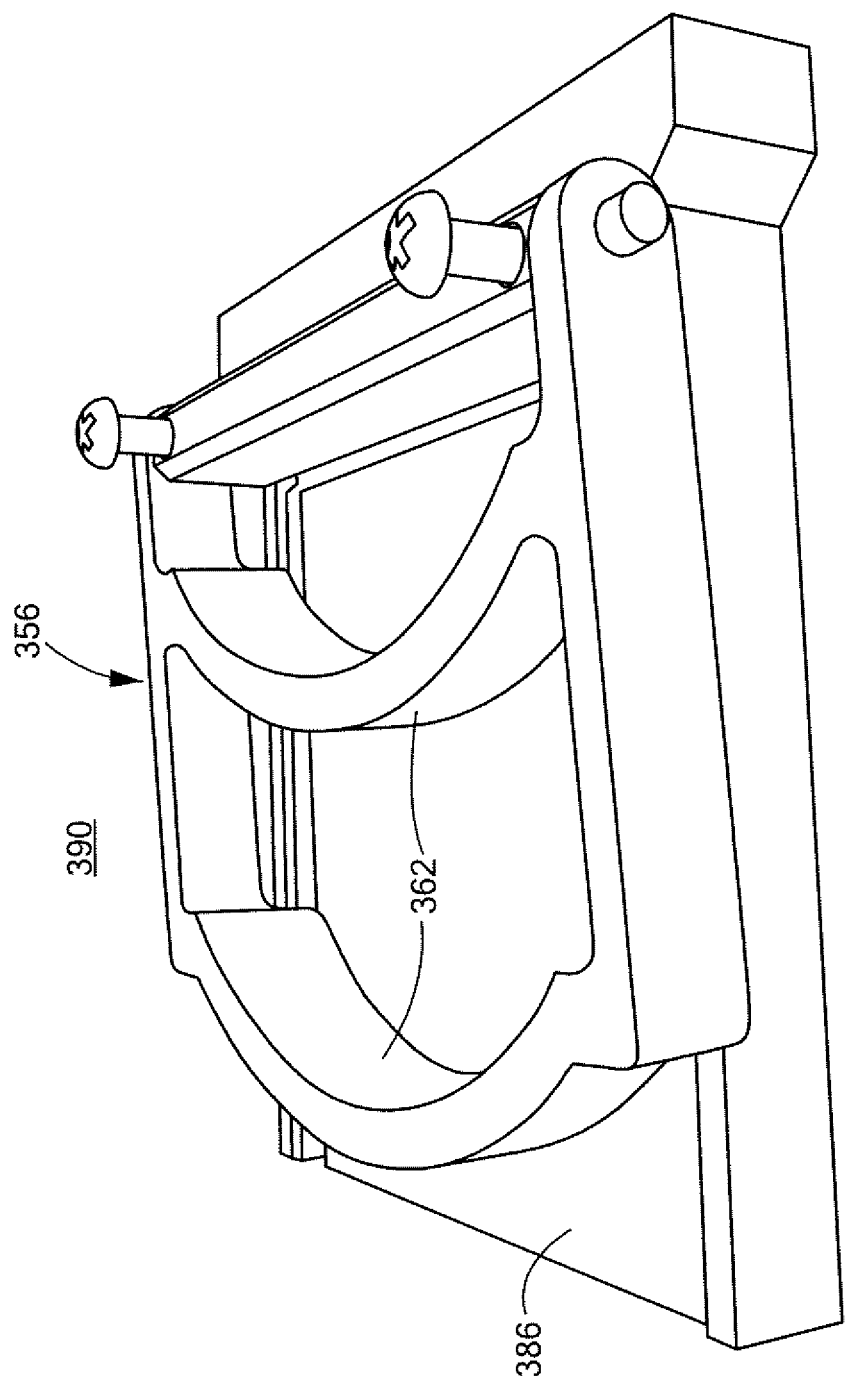
Figure 19:
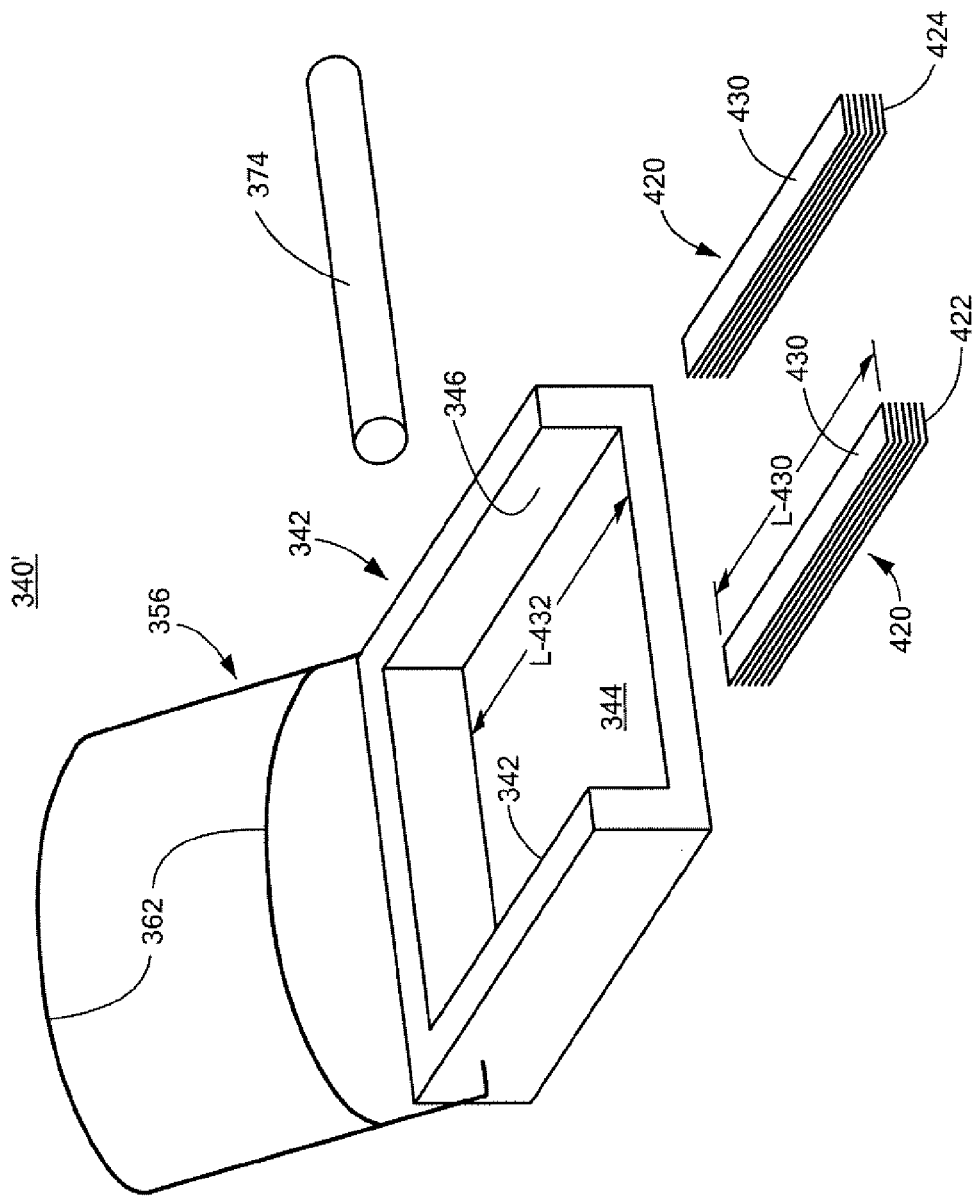
FIGS. 19-20 show an example of another method for manufacture the array of hollow fiber shown in FIGS. 4, 5A-5C, and 6 in accordance with this invention.
Figure 20:
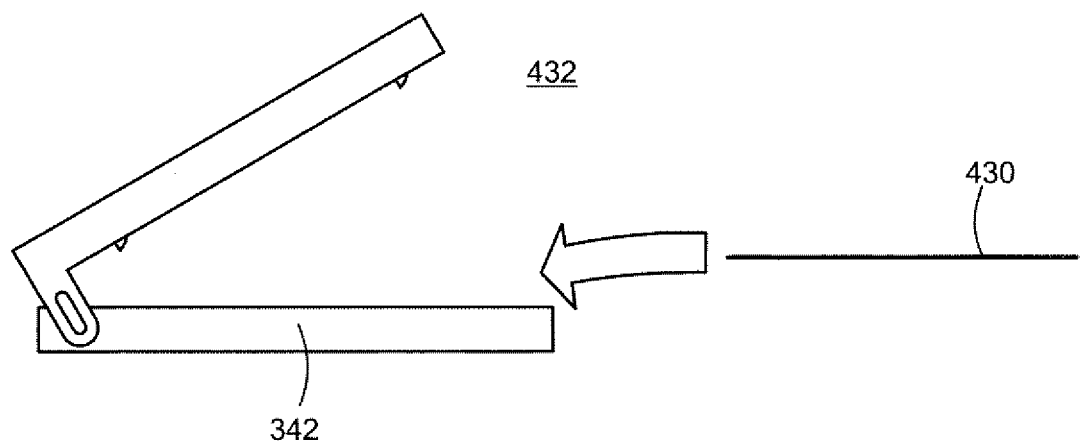

In another embodiment, system 340, FIG. 19 includes a plurality of smaller shims 420, FIG. 19, having a length L-430 approximately equal to length L-342 of sides 346. In one example, plurality of shims 420 may be placed in two stacks 422 and 424. Then, one shim from each stack of shims 422, 424, e.g., top shim 430 is placed against opposing sides 346 in bed 344, step 432, FIG. 20. A layer of hollow fibers is then placed between the opposing shims. Adhesive 382, FIG. 12, is applied to contact surface 366 on blades 362, similar to step 384, FIG. 12. Applicator 356 is then lowered over the co-planar layer of opposing shims and layer of hollow fibers 32 therebetween to apply adhesive 382 to the shims and layer of hollow fibers. Applicator 356 is then raised. Adhesive 382 is then rolled away from the center portion of the layer of hollow fibers using roller 374, FIG. 9, similar to step 394, FIG. 15. Roller 374 uniformly distributes the adhesive over the increasing height of the array using the two opposing sets of opposing shims against sides 346 as support. As the array of hollow fibers 32 forms with each new layer of fibers, the adding of the opposing layers of shims allows for the rolling height to stay relatively constant. After the array is completed, it is then cut along the adhesive to a desired shape, similar as discussed above with reference to FIGS. 17 and 18.

Although, as discussed above with reference to FIGS. 8-20, the steps of manufacturing various embodiments of array 30 of hollow fibers 32 may be depicted in a certain order, this is not a necessary limitation of this invention, as the steps of manufacturing array 30 may be performed in one or more different orders as known by those skilled in the art. Additionally, the adhesive applicator need not necessarily be pivotably attached to the base. In this design, the adhesive applicator vertically descends and is receivable in the bed or base such that the adhesive applicator with adhesive thereon applies adhesive to the appropriate places to the fibers, similar as discussed above.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:
1. An array of hollow fibers comprising:
    a plurality of hollow fibers of a predetermined diameter configured to receive a gas having oxygen therein and transfer the oxygen to a fluid and/or transfer carbon dioxide from the fluid to the gas; and a plurality of headers having a plurality of recesses configured to receive the plurality of hollow fibers, wherein the plurality of headers is configured to align the plurality of hollow fibers in a predetermined regular pattern having a predetermined packing density that is a fraction of a total cross-sectional area of the array occupied by the hollow fibers, in which array the hollow fibers are aligned such that spacing between the hollow fibers is relatively constant along the length of the array.

2. The array of claim 1 in which the array is configured such that the distance between the hollow fibers is less than or substantially equal to the predetermined diameter.

3. The array of claim 1 in which the fraction is in the range of 0.20 to about 0.90.

4. The array of claim 1 in which the plurality of hollow fibers are configured in a hexagonal arrangement.

5. The array of claim 4 in which the plurality of hollow fibers is configured to be hexagonally closely packed.

6. The array of claim 1 in which the plurality of headers comprises a first end-header having a plurality of recesses on one side configured to receive a first layer of the plurality of hollow fibers;

a second end-header having a plurality of recesses on one side configured to receive a second layer of the plurality of hollow fibers; and a plurality of mid-headers having a plurality of recesses on both sides configured to receive the plurality of hollow fibers, wherein a first of the plurality of mid-headers is configured to receive the first layer of the plurality of hollow fibers such that the first layer of the plurality of hollow fibers is sandwiched between the first end-header and the first of the plurality of mid-headers, and wherein a second of the plurality of mid-headers is configured to receive the second layer of the plurality of hollow fibers such that the second layer of the plurality of hollow fibers is sandwiched between the second end-header and the second of the plurality of mid-headers.

\* \* \* \* \*